US009301870B2

(12) United States Patent
Shelton et al.

(10) Patent No.: US 9,301,870 B2
(45) Date of Patent: Apr. 5, 2016

(54) URINARY DEVICE HAVING ANTISEPTIC AND HEALTH TESTING PROPERTIES

(75) Inventors: Michael Shelton, Harrow (GB); Peter Maxwell, London (GB); Graheme Gunns, Harrow (GB)

(73) Assignee: Aim-Straight Ltd., Middlesex (GB)

( * ) Notice: Subject to any disclaimer, the term of this patent is extended or adjusted under 35 U.S.C. 154(b) by 519 days.

(21) Appl. No.: 12/759,993

(22) Filed: Apr. 14, 2010

(65) Prior Publication Data

US 2010/0263113 A1  Oct. 21, 2010

(30) Foreign Application Priority Data

Apr. 16, 2009 (GB) .................................. 0906536.8

(51) Int. Cl.
*A47K 11/00* (2006.01)
*A61F 5/453* (2006.01)
*A61B 10/00* (2006.01)

(52) U.S. Cl.
CPC ......... *A61F 5/453* (2013.01); *A61B 2010/0003* (2013.01)

(58) Field of Classification Search
CPC ............ A61F 5/4556; A61F 13/49473; A61B 10/007; A61B 2010/0003
USPC ........ 4/144.1–144.4; 604/327–330, 358, 378, 604/385.201, 544; 600/574, 573, 584
See application file for complete search history.

(56) References Cited

U.S. PATENT DOCUMENTS

| | | | | |
|---|---|---|---|---|
| 1,646,121 A * | 10/1927 | Thorp | ............................. | 221/63 |
| 2,865,718 A | 12/1958 | Fowler | | |
| 2,878,486 A | 3/1959 | Bartlett et al. | | |
| 4,408,905 A * | 10/1983 | Ehrenkranz | .................... | 374/157 |
| 4,756,029 A * | 7/1988 | Zieve et al. | ..................... | 4/144.4 |
| 4,937,890 A * | 7/1990 | Tafur | ..................... | A61F 5/4556 4/144.1 |
| 5,370,637 A * | 12/1994 | Brodeur | ......................... | 4/144.3 |
| 5,408,703 A * | 4/1995 | Cicio | ..................... | A47K 11/12 4/144.2 |
| 5,409,315 A * | 4/1995 | Evans | ..................... | B65D 65/46 383/1 |
| 5,605,161 A | 2/1997 | Cross | | |
| 5,966,748 A * | 10/1999 | Young | ..................... | A47K 11/12 4/144.4 |
| 6,202,225 B1 * | 3/2001 | Beck | ..................... | A61F 5/4556 141/337 |
| 6,327,716 B1 * | 12/2001 | Kaus | ..................... | A61F 5/4556 4/144.4 |
| 6,460,200 B1 * | 10/2002 | Mottale | ................. | A61F 5/4556 141/331 |
| 6,546,566 B1 * | 4/2003 | Geisel | ............................ | 4/144.1 |
| 6,620,142 B1 | 9/2003 | Fluckiger | | |

(Continued)

FOREIGN PATENT DOCUMENTS

DE  4343789  5/1995
DE  10101679  7/2002

(Continued)

*Primary Examiner* — Lauren Crane
*Assistant Examiner* — Erin Deery
(74) *Attorney, Agent, or Firm* — Berliner Steffin Azod LLP

(57) ABSTRACT

A urinary directional device for improving the directional urination and health of a male user is provided, in which the device comprises a conduit for the passage of urine and having a proximal end adapted for engagement with the penis of the user and a distal end having a distal aperture to enable the passage of urine from the conduit, the device having an interior surface providing one or more of a cleansing, an antibacterial or antiseptic or an anti-fungal function whereby the penis of the user can be cleansed by wiping on the interior surface of the device after urination and the device optionally further comprising a health detection indicator capable of indicating abnormalities in urine indicative of disease or health-related conditions.

20 Claims, 1 Drawing Sheet

(56) References Cited

U.S. PATENT DOCUMENTS

| | | | |
|---|---|---|---|
| 6,719,741 B2 * | 4/2004 | Ching | A61F 5/4556 604/329 |
| 7,171,699 B2 * | 2/2007 | Ernest et al. | 4/144.2 |
| 2003/0149408 A1 | 8/2003 | Levinson | |
| 2003/0195483 A1 | 10/2003 | Ching | |
| 2007/0044213 A1 * | 3/2007 | Hall | A61F 5/4556 4/144.4 |

FOREIGN PATENT DOCUMENTS

| | | |
|---|---|---|
| EP | 1055402 | 11/2000 |
| ES | 2181547 | 2/2003 |
| FR | 2742981 | 12/1995 |
| GB | 2361871 | 11/2001 |
| GB | 2392842 | 3/2004 |
| GB | 2396819 | 7/2004 |
| GB | WO 2005094691 A1 * 10/2005 ........... A61B 10/007 |
| JP | 10-234763 | 9/1998 |
| JP | 2000034764 | 2/2000 |
| JP | 2001-161734 | 6/2001 |
| WO | WO 00/15166 | 3/2000 |
| WO | WO 02/38088 | 5/2002 |
| WO | WO02/094104 | 11/2002 |
| WO | WO 2004/028322 | 4/2004 |
| WO | WO 2008/013560 | 1/2008 |

* cited by examiner

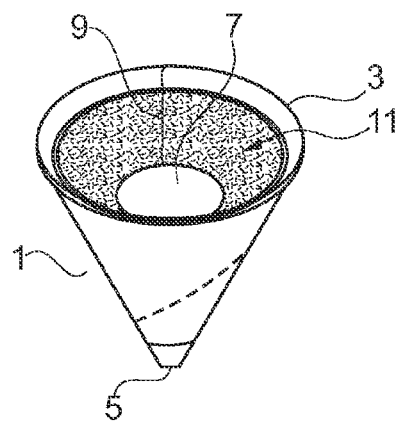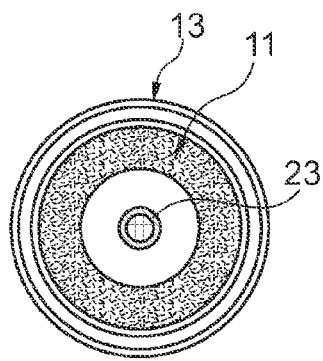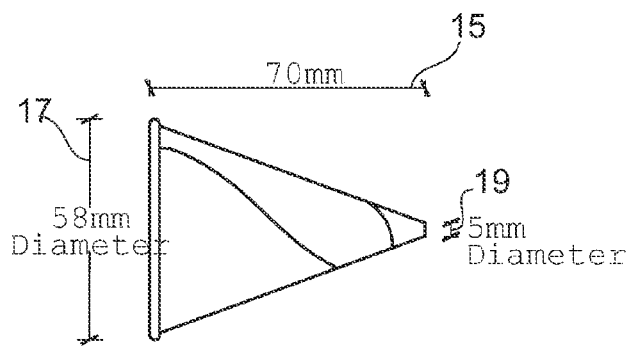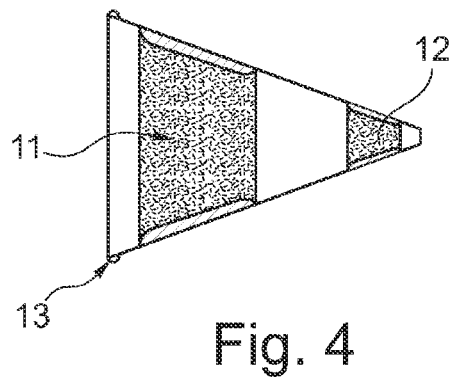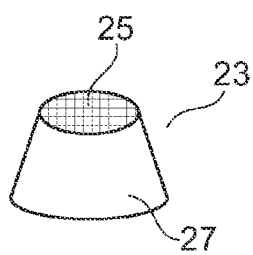

URINARY DEVICE HAVING ANTISEPTIC AND HEALTH TESTING PROPERTIES

FIELD OF THE INVENTION

The invention relates to a device for improving accuracy and hygiene during urination, which incorporates a means for detecting disease or illness through in situ urine testing. The invention, in particular, relates to the provision of a urinary directional device for use by men when urinating standing up, which device has the effect of improving the hygiene of this procedure. The invention further relates to a method of manufacturing such a device.

BACKGROUND OF THE INVENTION

In public and domestic toilet facilities, it is a common problem that spillage and misdirection during urination by an individual causes unpleasant and unhygienic stains and odours around the edges of the toilet or urinal, the surrounding floor area and even minor urine stains to the clothing of the individual. This is particularly a problem with children or the infirm or in toilets in public transport where the motion of the vehicle makes accuracy more difficult. A further problem is that where conventional toilet and hand washing facilities are not available, even if using a urinary directional device, there typically no opportunity to wipe up or hand wash which causes unpleasant staining or odour in clothing.

Several potential solutions to at least the former problem have been proposed, although no entirely satisfactory solution exists, some of which are described below.

JP 10-234763 discloses a male urination adjustment cylinder for correcting an orbit when males of advanced age urinate. The device described is cylindrical with a tapered distal end for discharge of urine. It is designed to be worn on the penis of the male urinating to improve directional flow and reduce soiling of the toilet bowl or clothing. The cylindrical portion includes a handle for the user to direct urination and to aid with application and removal. The described device, however, has the disadvantage that it has to be fitted substantially on to the penis which is a fiddly procedure and it does not address the hygiene issues of wiping or mopping excess urine remaining on the penis.

JP 2001-161734 describes an alternative solution to assist in directional urination for the male. Rather than the male wearing the device on his penis during urination, this document describes a guide cylinder of conical or other funnel-like configurations which is supported in a support structure positioned above the toilet bowl so that urination into the funnel will reduce scatter and avoid soiling of the toilet bowl or trousers. The guide cylinder portion may be disposable and formed of water dissolvable paper or may be reusable and formed of polyethylene or polypropylene to enable a light-weight element that is repeatably washable. The guide die typically has a length of from 10 to 50 cm, a large opening diameter of form 10 to 40 cm and a small opening diameter of 1 to 5 cm. The support structure portion consists of a movable arm attached at one end via a hinge to the under side of the toilet lid or to a wall via an extendable arm and having at the other end a retaining ring for supporting the cylinder guide portion. The support structure may be fitted with a non-slip material such as rubber, or a clamp, to reduce slippage of the guide cylinder portion in the support. There is no disclosure in JP 2001-161734 of the structure being movable such that the guide cylinder is in contact engagement with the penis and as such there is still the potential for the urine to spray or miss the funnel. The assembly also has additional hardware (e.g. the support structure or the funnel itself is reusable) which has the potential for gathering spilled urine and becoming a hygiene hazard itself. Furthermore, the document does not address the wiping of excess urine from the penis and surroundings nor does it provide for any anti-bacterial or anti-fungal function.

ES 2181547 describes a single use or disposable male urination device with a wall dispenser. The device is designed to prevent staining of the floor and surroundings and resulting bacteria and odour when men urinate standing up. The device, which is formed of a slightly waterproofed (e.g. by compression or waxing) cellulose or paper adapter, consists of a truncated cone which extends as a cylinder to form a one-piece Y-shaped form, or alternatively a simpler truncated V-shaped cone or a cylinder, which leads urine from the penis to the toilet. The described device is of length in the region of 50 cm, which in the case of a Y-shaped device is typically 25 cm of truncated cone and 25 cm cylinder portion. The large diameter opening, in which the penis engages, is typically about 5 cm whilst the small diameter opening is typically about 1.5 cm. A range of dispenser arrangements are described, including a stack of inter-stacking guide cylinders and a role of connected devices in a dispenser. A disadvantage of the device described in ES 2181547 is the length of the device may make it awkward to use and would increase the volume of residual urine in the device after use. There is no mention in this document as to the improvement of hygiene by wiping excess urine from the penis or any anti-bacterial function.

EP 1055402 discloses a female urinary device to allow women to urinate in an upright position. It comprises a foldable tubular body which in use assumes a reverse truncated pyramid form in which the apertures are preferably quadrangular or rhomboidal in shape. The purpose of the device is to enable females to urinate in a standing position, in particular to avoid contact with toilets in public conveniences which may not be hygienic. The device is preferably disposable, for hygiene reasons, but may be formed of material enabling reuse. The device is made of a material, e.g. paper or card, having a water impermeable or water repellant coating.

Several other disclosures, including GB 2361871, WO 2004/028322, WO 00/15166 and GB 2396819 describe urine directional devices, which may be disposable or reusable, typically designed to assist women in urinating standing up.

Several prior art documents propose potential solutions to assist in reducing spraying and improving directional urination for men (and women) when urinating standing up. However, several of these potential solutions have disadvantages associated with them, such as the excessive length of the funnel. Furthermore, there is no adequate means to enable improved directional flow in men and thereby reduce spraying when urinating standing up whilst providing improved hygiene to the user.

A further problem related to health is early detection of diseases which can improve prognosis and prevent a condition worsening. Men in particular are reluctant to visit doctors or medical centres for regular check-ups. An easy means for providing early detection of various conditions is desirable and is preferably achieved by urine testing.

Urine test strips are readily available and commonly used in clinics for testing for a range of conditions, such as diabetes, liver disease, kidney function and bacterial infections amongst others. A regular problem that has been identified in urine dip tests is that of providing a suitable sample and hygienically filling a sample bottle, particularly for women. Accordingly, there has been much effort in providing suitable sample collecting devices. US2003/0149408, for example, describes a urine sample collection apparatus for use by a woman without sitting on a toilet, which comprises a body-contacting aperture through which the woman will urinate, a first outlet aperture to which is removably secured a sample bottle and a second outlet aperture which may be directed to a toilet or a second collection bottle. By this means, urine may be collected in the first sample bottle and when full, the urine stream automatically passes to the second outlet.

Devices for in situ testing in the sample collection process have also been proposed.

U.S. Pat. No. 5,605,161 describes a disposable urinalysis device which is for use by males and females to urinate whilst in an upright position while preventing soiling of the body or clothing. The device is in the form of a cone or funnel which may be stored in a collapsed, compact profile and when addressed for use is dimensioned to envelop the exterior of the female vaginal area. It is fitted urinalysis test strips which after exposure to urine are detached from the device for urinalysis. The urinalysis test strips may be fitted to the device by fixing a urinalysis reagent ring at the distal end of the device which is configured to carry one or more urinalysis test strips, or providing them in a pouch on the exterior surface and attached with string whereby they can be disposed inside the cone or funnel prior to use. In this example, it is required to remove the test strip from the cone or funnel in order to assess the result.

GB-A-2392842 describes a urinary device provided as a flat sheet of material of teardrop shaped cross-section which may be fastened along the side edges to form a tubular urinary device. The urinary device may further comprise a reagent test strip, capable of indicating the presence or absence of a substance in the urine by a colour change in the test member. It is provided that the test strip be visible so that it is not necessary to handle urine-contaminated test strip in order to assess the result. Accordingly, it is preferred according to GB-A-2392842 that the test member is formed on the outer wall of the device or is formed on an internal wall at a region provided with a transparent material or window so that it can be viewed externally. The test member may be attached to the urinary device by welding to the interior, by using an adhesive or by forming a slot on the interior of the urinary device to receive the test member.

There is no disclosure of providing a coating on or impregnating into a urinary directional aid a reagent material capable of indicating the presence or absence of substances indicating a disease or bodily condition, e.g. by colour change. There is further no disclosure of providing in the urinary directional aid a means internal to the device to wipe excess urine from the penis and provide a cleansing (e.g. anti-bacterial or anti-fungal) function on the penis.

PROBLEM TO BE SOLVED BY THE INVENTION

There is therefore a problem of providing a urinary directional device that provides improved independence and hygiene for the user.

It is an object of this invention to provide such a device which enables the hands and urinogenital area of the user to remain hygienically clean or cleansed.

It is a further object of the present invention to provide a device that can be discarded at the site of use and reduce any bacterial build up or discomfort for the user.

It is a still further object of the present invention to provide a means for early warning of disease or bodily health-related condition which will alert the user of the need to see a doctor or medical professional about possible treatment or avoidance of a medical or health condition.

SUMMARY OF THE INVENTION

In accordance with a first aspect of the invention, there is provided a urinary directional device for improving the directional urination of a male user, said device comprising a conduit for the passage of urine and having a proximal end adapted for engagement with the penis of the user and having a proximal aperture to enable the passage of urine into the conduit and a distal end having a distal aperture to enable the passage of urine from the conduit, said device having an interior surface and an exterior surface, the device being characterized in that the interior surface provides one or more of an anti-bacterial or antiseptic or an anti-fungal function whereby the penis of the user can be cleansed by wiping on the interior surface of the device after urination.

In a second aspect of the invention, there is provided a urinary directional device comprising a conduit for the passage of urine and having a proximal end adapted for engagement with the urogenital area of the user and having a proximal aperture to enable the passage of urine into the conduit and a distal end having a distal aperture to enable the passage of urine from the conduit, said device having an interior surface and an exterior surface, the interior surface providing one or more of a cleansing, an anti-bacterial or antiseptic or an anti-fungal function (and/or other medically active function such as anti-viral function) whereby the urogenital area of the user can be cleansed by wiping on the interior surface of the device after urination, the device further characterized in that it further comprises a health detection indicator capable of indicating abnormalities in urine indicative of disease or health-related conditions.

In a third aspect of the invention, there is provided a urinary directional device comprising a conduit for the passage of urine and having a proximal end adapted for engagement with the urogenital area of the user and having a proximal aperture to enable the passage of urine into the conduit and a distal end having a distal aperture to enable the passage of urine from the conduit, further having a distal portion characterized by providing for the passage of a stream of urine and a proximal portion, which during urination does not come into substantial contact with the stream of urine, said device characterized in that it is provided with one or more reagent compositions coated onto or impregnated into the distal portion of the device, the reagent compositions being capable of indicating one or more abnormalities in the urine that are indicative of disease and/or health-related conditions.

In a fourth aspect of the invention, there is provided a urinary directional device comprising a conduit for the passage of urine and having a proximal end adapted for engagement with the urogenital area of the user and having a proximal aperture to enable the passage of urine into the conduit and a distal end having a distal aperture to enable the passage of urine from the conduit, further having a distal portion characterized by providing for the passage of a stream of urine and a proximal portion, which during urination does not come into substantial contact with the stream of urine, said device characterized in that it is provided in the distal portion with a screen or grill capable of allowing fluid to pass through the distal aperture.

In a fifth aspect of the invention, there is provided a disposable insert for a urinary directional device, the device having a conduit for the passage of urine, a proximal end adapted for engagement with the urinogenital area of the user, a proximal aperture to enable the passage of urine into the conduit, a distal end having a distal aperture for the passage of urine from the conduit and having a distal portion characterized by providing for the passage of a stream of urine and a proximal portion, which during urination does not come into direct contact with the stream of urine, said disposable insert being adapted to removably fit about and/or inside the proximal end of the device and characterized by providing one or more of the following:

A) over at least a part of the proximal portion of the device an anti-bacterial, antiseptic or anti-fungal function whereby the urinogenital area of the user can be cleansed by wiping with the at least part of the proximal portion after urination;

B) over at least a part of the distal portion of the device a health detection indicator configured to receive passage of urine during use and being capable of indicating abnormalities in urine indicative of disease or health-related conditions, wherein the health detection indicator is provided by one or more reagent compositions impregnated into and/or coated onto the interior surface of the insert; and C) in the distal portion of the device a screen or grill capable of allowing fluid to pass through the distal aperture.

In a sixth aspect of the invention, there is provided a method of manufacturing a urinary direction device or a disposable insert as described above, said method comprising providing in sheet form a material with which to form the device, impregnating or coating at least a portion of said material with an anti-bacterial or anti-fungal agent, cutting said sheet material and assembling therefrom the device.

In a seventh aspect of the invention, there is provided a stacking assembly of the device or the disposable insert as defined above, said assembly comprising a dispensing component for dispensing said devices and a plurality of said stacked devices or inserts.

ADVANTAGES OF THE INVENTION

The present invention enables improved directional control of urination by men or women when urinating standing up, whilst also improving hygiene by enabling the user's urogenital to be cleansed by a portion of the device having a cleansing, anti-bacterial/antiseptic and/or anti-fungal function (and/or other medical function such as anti-viral function) and optionally provides an early disease detection means by way of a urinalysis function. By having the cleansing, anti-bacterial and/or anti-fungal function (and/or other medical function such as anti-viral function) located at specific portions of the device, the cleansing action can be performed on the user simply by the action of removing the device after use. This has a particular benefit of reducing the likelihood of infection and improving sexual health. By providing the a health detection indicator capable of indicating abnormalities in urine indicative of disease or health-related conditions as an integral part of the device or insert therefore, the user can be alerted to potential health problems at an early stage and in the normal course of activities prompting them to seek medical advice and thereby improving disease prognosis. In particular, the device, for example where provided with anti-bacterial function and bacterial infection indicator (e.g. the bacteria *Chlamydia trachomatis*), may be capable of reducing the incidence of cervical cancer in the female sexual partners of (male) users of the device (especially uncircumcised users) since such infections sexually transmitted are believed to be a risk factor in the contraction of cervical cancer. Further, the device reduces spillage and soiling of the area surrounding a toilet or urinal and of the user's clothing as well as improving the personal hygiene of the user.

BRIEF DESCRIPTION OF THE DRAWINGS

FIG. 1 is an aspect view of a directional urinary device of the present invention;

FIG. 2 is a plan view of the directional urinary device depicted in FIG. 1;

FIG. 3 is a side view of the directional urinary device depicted in FIG. 1;

FIG. 4 is a cross sectional view from A-B of the directional urinary device depicted in FIG. 3;

FIG. 5 is an aspect view of a disposable insert for use with a directional urinary device of FIG. 1.

DETAILED DESCRIPTION OF THE INVENTION

The device according to the present invention may be used in any location as and when required. It is particularly useful for directional urination into a urinal or toilet bowl in domestic or public conveniences, where cleanliness and hygiene issues result from directional errors during urination. It also provides the additional benefits of hygienic absorbency or anti-bacterial function for the user and the passive detection or indication of the presence of disease, illness, poor health or negative condition. Typically, an optional health indicator provides its indication by way of colour change of a reagent.

In general, the invention provides a urinary directional device, for improving the directional urination of the user, or an insert for such a device, which is adapted for engagement with the urinogenital area of the user, which device or insert preferably has on at least a portion thereof an anti-bacterial/antiseptic/anti-fungal and/or absorbent function whereby the user can wipe excess urine from the urinogenital area on removal following urination. Additionally or alternatively, the device or insert provides a health detection indicator which is capable of indicating abnormalities in urine which abnormalities may be indicative of disease or health-related conditions. The health detection indicator is preferably provided by means of one or more reagent compositions capable of reacting with components present in the urine and which provide an indication such as a colour change when such components are present in abnormal amounts which indicate disease or illness.

For further describing the invention and its various embodiments hereinafter, the terms proximal and distal shall be used to refer to positions on the device or insert relative to the user during use of the device.

The urinary directional device comprises a conduit for the passage of urine, has a proximal end adapted for engagement with the urinogenital area of the user and a proximal aperture to enable the passage of urine into the conduit and a distal end having a distal aperture to enable the passage of urine from the conduit. The device may further be defined as having a distal portion characterized by providing for the passage of a stream of urine and a proximal portion, which during urination does not come into substantial contact with the stream of urine. The device has an interior surface and an exterior surface. By interior surface, it is meant the surface defining an internal volume formed in the device by covering the distal and proximal apertures with a planar surface.

The device of the invention may be used, according to its configuration, by a man or a woman. The device finds particular application when configured for use by a man, whereby it is configured to receive the penis in the proximal end, since its key function as a passive indicator or early-warning function is most useful for people who regularly urinate standing up rather than on rare occasions or simply for the purpose of testing. Further, men are typically less inclined to visit the doctor or clinic for check-ups and as such symptoms and medical conditions can go un-noticed otherwise. Also, in its preferred embodiment, where the device provides a cleansing or antibacterial function as well as health-related indicator, there is a dual function of improving personal hygiene and sexual health as well as indicating at an early stage potential health problems for the user. Nevertheless, a device according to the present invention can be configured for use by a woman and the following details relating to the content and function of the cleansing composition and more particularly the health detection indicator formulations may apply also to such a device configured for use to assist a woman urinating standing up.

Accordingly, in the device aspects of the invention, there is an embodiment where the devices or inserts can be adapted for use by a man or adapted for use by a woman, which embodiments differ in particular by the shape of the proximal end for adaptation to fit about the urinogenital area of a man as compared to a woman.

According to the less preferred embodiment in which the device is configured for use by a woman, the device may be shaped the device may be shaped such as to provide engagement of the proximal aperture about the urinogenital area of the female whilst directing the flow of urine downward and away from the body. Preferably, it is shaped to the inverse of the contour of the external parts of the urinogenital area (e.g. to fit about the labia majora, especially laterally and posterior to the labia majora). Optionally, the shape of the device is open to choice provided the proximal aperture may be fitted to form a snug fit about the urinogenital area and the distal aperture is thereby positioned to direct urine away from the body. Preferably, according to this embodiment, the proximal aperture is defined by a rim that is irregular and preferably elliptical and the conduit is directed downward but angled forward in the direction of the ellipse (to the fore, when in use). It is particularly preferred that the rim of the proximal aperture should further define a tab (or lip) located one the periphery of the ellipse on the opposing end to the direction in which the conduit is directed which provides additional support and an enhanced seal on engagement with the posterior of the urinogenital area of the female (e.g. in the region between the urethra and the anus, i.e the perineum). Preferably, such a tab may form at least part of the proximal portion of the device which provides an absorbent, anti-bacterial/antiseptic and/or anti-fungal function which can be wiped along the urinogentital area of the female on removal of the device (noting that for this embodiment of the invention adapted for use by a female, the cleansing, anti-bacterial, antiseptic or anti-fungal function is provided on a tab or extended portion of the device at the proximal end rather than necessarily on the interior surface of the device as otherwise defined herein). In any case, the absorbent, anti-bacterial/antiseptic and/or anti-fungal function is preferably provided in a proximal portion of the device toward the rear (in use) of a rim defining the proximal aperture (and optionally around the entire rim) in order that the absorbent, anti-bacterial/antiseptic and/or anti-fungal effect can be felt upon removal of the device after use. Suitable shapes for a device according to the invention also include those such as are described in WO 2005/089687 (especially the figures), WO 2004/028322 (esp. FIGS. 1-4), GB 2396819 (especially the figures) and GB 2361871 (especially the Figures), the disclosures of which are incorporated herein by reference. The device of the present invention, in those embodiments incorporating the shape of devices described in prior inventions, is characterized by having at least part of a proximal portion providing an adsorbent, anti-bacterial/antiseptic and/or anti-fungal function, which contacts or is easily contacted with the urinogenital area of the user upon removal of the device.

In a device according to the preferred embodiment of the invention in which the device is adapted and configured for use by a male user urinating standing up, the internal surface preferably provides one or more of a cleansing, an anti-bacterial or antiseptic or an anti-fungal function. This is preferably achieved by coating and/or impregnating the interior surface with a formulation or composition having said function. Preferably, at least part of the proximal portion provides one or more of a cleansing, an anti-bacterial or antiseptic or an anti-fungal function whereby the user's penis can be cleansed by wiping with the at least part of the proximal portion after urination.

Similarly, in the aspect of the invention which provides an insert into a reusable urinary directional device having a conduit for the passage of urine, a proximal end adapted for engagement with the urinogenital area of the user, a proximal aperture to enable the passage of urine into the conduit, a distal end having a distal aperture for the passage of urine from the conduit and having a distal portion characterized by providing for the passage of a stream of urine and a proximal portion, which during urination does not come into direct contact with the stream of urine, the insert is adapted to removably fit about and/or inside the proximal end of the device and provides over at least a part of the interior surface of the insert, preferably at least part of the proximal portion of the device a cleansing, an anti-bacterial/antiseptic or an anti-fungal function whereby the user's penis can be cleansed by wiping with the at least part of the proximal portion after urination.

The directional device according to the invention may be disposable or may be a reusable device fitted with the described disposable insert. It is a preferred feature of the invention that at least the soiled portion of a urinary directional device is used once and then disposed of after soiling. Similarly, the anti-bacterial/antiseptic or anti-fungal or absorbency features of the invention are intended for a single use.

As can be seen from the above, there are two aspects of the invention—a urinary directional device and an insert for a urinary directional device, which device and/or insert provide an anti-bacterial/antiseptic and/or anti-fungal and/or absorbency function (and/or other medical function such as an anti-viral function), whereby the user's penis can be cleansed on removal of the device after urination and/or a health detection indicator function.

In the description that follows, the text shall refer to the urinary directional device according to the first aspect of the invention. However, where the context allows, it is intended also to refer to an insert for such a urinary directional device.

In an embodiment of the invention, the urinary directional device (or the insert therefore) is adapted for use by a man when urinating to improve directional accuracy whilst providing a passive health detection indicator function. The device finds particular benefit for use by uncircumcised males, since directional aim is more difficult and there is a greater likelihood of a build up of bacteria or fungal infection, or even presence of viral infection, associated with the foreskin and the application of improved hygiene in this way can reduce the risk of developing infection. According to this embodiment, the proximal end is of a shape and dimension to allow the tip of the penis to fit, preferably snugly, within the proximal aperture and engage with the device (preferably so as to form a loose seal about the circumference of the penis)

to allow, during urination, passage of urine through the conduit of the device and out the distal aperture. The proximal aperture may therefore be of any suitable shape with sufficient overall dimension, such as a quadrangle, pentagon, hexagon, a fluted shape or preferably an elliptical or circular shape to provide a better engagement.

The overall shape of the device according to this embodiment may be any suitable shape. For example the device may be an inverted pyramid (the larger end of which pyramid is the proximal end of the device) of triangular, quadrangular, pentagonal, hexagonal or other form or alternatively a fluted arrangement to encourage passage of urine rapidly through the conduit or a conical form. The device may further comprise of a conical or inverted pyramidal shape with a cylindrical or further pyramidal distal extension. Preferably, the device is a truncated conical (or frusto-conical) form in which the proximal aperture is formed as the base of the cone and the distal aperture is defined by the truncated peak of the cone.

The cleansing and/or anti-bacterial/antiseptic and/or anti-fungal function may be provided in any suitable arrangement on the interior surface, preferably on the proximal portion of the device. Preferably, it is provided such that on removal of the device by the male user, that part of the proximal portion comes into direct contact with the external terminus of the urethra and surrounding area providing an absorbency and/or cleansing effect. In one embodiment in which the device is substantially frusto-conical in shape, the absorbent and/or anti-bacterial/antiseptic and/or anti-fungal function is provided in a part of the proximal portion of the device which extends largely or more preferably fully around the interior surface of the device (e.g. in a frusto-conical form) to enable the benefit to be effected irrespective of the rotational positioning of the device by the user. Preferably, the longitudinal dimension (i.e. in the direction of the axis of the conduit) of the coating is in the range of from 10 to 50 mm, more preferably 15 to 30 mm. In another embodiment the entire interior surface (or internal face) is provided with the cleansing, anti-bacterial/antiseptic and/or anti-fungal function, preferably by coating or impregnation with a formulation or composition having such property.

Optionally, the device may further comprise of an extended tab (extending externally from the aperture, defined by a rim to the aperture), which in use may be positioned to the underside of the penis and optionally may be absorbent and/or anti-bacterial/antiseptic whereby on removal of the device after use, the tip of the penis may be cleansed further. Such a tab has the further benefit of increasing the ease of removal of the device from a stack (where the devices are dispensed from the proximal end of the device) or reducing the risk of multiple dispensing (where the devices are dispensed from the distal end of the device). For simplicity of manufacturing, however, it is preferred that no such tab is provided.

Optionally, the cleansing and/or anti-bacterial/antiseptic and/or anti-fungal function may also be provided on the exterior surface of the device to enable the hands of the user to be cleansed or kept sanitary.

The health detection indicator, capable of indicating abnormalities in urine indicative of disease or health related conditions is preferably a function that is provided in the distal portion of the device and preferably on the interior surface of the device and/or about the distal extremity of the device (interior and exterior) such that urine passing through the device contacts with the health detection indicator portion.

The health detection indicator is preferably provided by one or more reagent compositions impregnated into and/or coated onto the distal portion of the device, preferably the interior surface. The reagent compositions, being capable of indicating one or more abnormalities in the urine that are indicative of disease or health-related conditions, may be provided in any suitable location on the distal portion of the device (typically on the internal face) and in any suitable configuration. For example, the reagent compositions may be provided to cover the entire interior surface of the distal portion of the device or may be provided in such a configuration as to form a ring about the interior surface of the device whereby urine inevitably contacts with the reagent composition to trigger a response.

The health detection indicator, and in its preferred form as one or more reagent compositions, is preferably capable of detecting the presence of one or more component in the urine at levels indicative of the presence of disease, risk of disease or of health-related condition, and at a predetermined level or concentration of such a component provide suitable indication to the user.

For example, the health detection indicator may be capable of detecting one or more of glucose, ketones, blood, haemoglobin, protein, nitrite, urobilinogen, bilirubin, leuocytes, pH, specific gravity, antibodies associated with infection, and hormones associated with the presence of disease in a body.

Indication of predetermined levels of components in the urine is preferably provided by means of a colour change. This is typically provided by means of an indicator or an indicator-coupled reagent. The indicator, or indicator-coupled reagents, that are contained in the one or more reagent compositions is dependent upon which substance(s) or component(s) is/are to be detected. However, any suitable indicator or indicator-coupled reagent may be used in accordance with this preferred embodiment in order to provide an indication of the substance or component and such indicator and/or reagent being present in sufficient quantities and concentrations as to provide an indication at certain pre-determined levels indicative of a problem. The amount of reagent necessary to indicate a problem associated with the detected component should be derivable by the skilled person according to the efficiency of the particular.

Accordingly, the devices according to the invention may optionally provide an indication for further investigation as to the presence in the user of one or more of diabetes, liver dysfunction, liver disease, liver failure, renal glycosuria, insufficient food intake or metabolism, kidney damage, urinary tract infection, kidney or balder calculi, myocardial infarction, muscle damage, bacterial infection, haematoma, cystitis, testicular cancer, prostate cancer and HIV infection.

Optionally, the health detection indicator provides a range of possible results through indication of the presence of an abnormal quantity of a specified substance or component, such as is typically provided by urinalysis reagent strips.

Preferably, however, the indicator provides qualitative rather than quantitative information, whereby indication is given only when the relative amounts of specified substance or component are such to indicate likelihood of a problem, which amounts would be apparent or calculable by a person skilled in the art. Thereby, one of two results may be provided by the health detection indicator on use of the device: if the concentration or amount of substance to be detected does not exceed a pre-determined 'danger' value (as determined during formulation with the assistance of a clinician), no colour change occurs; if the concentration or amount of substance to be detected exceeds the pre-determined 'danger' value, a detectable colour change occurs indicating to the user that they should seek further investigation.

Examples of suitable indicators may be as follows.

A glucose indicator, which may indicate the presence of high levels of glucose (e.g. in excess of 15 mg glucose per dl of urine) associated with renal problems of diabetes, may be for example a sequential enzyme reaction indicator. This may comprise a glucose oxidase to oxidize glucose to gluconic acid and peroxide, and a peroxidase catalysis reaction of peroxide with potassium iodide to provide a colour change indication of a problem.

Ketones in the urine, which is indicative of a range of possible problems including stress and infection but specifically diabetes, may be detected for example by the reaction of acetoacetic acid in urine with nitroprusside, the colour change occurring when any ketone is detected (since the normal incidence in urine is zero).

Blood in urine, which may be indicative of haematuria (kidney or bladder calculi or damage to the kidney or urinary tract), haemaglobulinuria (breakdown of red blood cells or poison) or myoglobinuria (myocardial infarction or muscle damage), may be detected for example based on the pseudoperoxidase activity of haemaglobin which catalyses the reaction of 3,3',5,5'-tetramethylbenzidene and a buffered organic peroxidase to provide a colour change.

Proteins may be detected for example based on the indication by tetrabromophenol blue.

Nitrites, which are indicative of urinary tract infection or other bacterial infection such as from *e coli, salmonella, citrobacter* etc, may be detected for example by the reaction of p-arsanilic acid and nitrite in urine to form diazonium compound which couples with an indicator. The presence of any nitrites should be investigated.

The presence or bilirubin, which is useful in indicating liver disease before presence of clinical symptoms, may be identified as a result of coupling of bilirubin with 2,4-dichlorobenzen diazonium salt to cause a colour change.

Human Chorionic Gonadotropin (HCG) hormone, which is indicative of testicular cancer and other forms of cancer, may be detected in urine by utilizing a monoclonal antibody that binds (preferably specifically) to beta-hCG as antigen and which is coupled to a colour change indicator. Such a system is described for example in WO2008/013560.

In detecting HIV, certain proteins or peptide sequences coupled to an indicator may be used to capture specified HIV antibodies in the urine.

These and various other suitable reagents are known in the art and may be used or adapted for use in the present invention.

Optionally, the health detection indicator, typically being a reagent formulation, is provided impregnated into a portion of the distal portion of the device designed as a form of reservoir for conducting the test. This may be achieved by means of a fluid absorbent area such as by padding material or, for example, by multiple micro-fluidic pores formed on the internal surface over a specified area in order to control the volume of urine from which the indicative test result is being achieved.

Preferably, the reagent composition may be provided as a dry powder formulation, e.g. onto the distal tip of the device, or by spraying the one or more reagents forming the reagent composition onto the corresponding portion of the device and allowing to dry, or any other suitable method of application.

The device may be provided with indicators for one or more substance or disease. For example, the device may be provided with a reagent composition comprising indicators and/or indicator-coupled reagents capable of detecting a range of substances or components associated with disease or ill-health, such as for example glucose, protein, nitrites, leukocytes and bilirubin. The configuration of such indicators or indicator-coupled reagents in the reagent composition as applied to the distal portion of the device may be varied. For example, all the reagents may be mixed to form a reagent composition which colour change indicates a problem associated with one or more of the identified substances or components. Alternatively, each reagent may be configured separately on the distal portion of the device, such as a series of concentric rings formed on the interior surface of the device, whereby a colour change at a specific position on the device is indicative of a problem corresponding to a specific substance or component to be identified. For the latter alternative, the user would need additional information to interpret the result as compared with the simpler 'problem' indicator.

Accordingly, the device may be provided as a disease-specific or substance-specific indicator, or alternatively may be provided as a general health indicator which is not specific to any particular disease or substance.

Depending upon the configuration of a reagent composition on the distal portion of the device, it may be useful to facilitate the viewing of the results. Colour change indication may be provided on the interior of the device. Optionally, the material of the device may be formed in certain regions of a material that is translucent whereby the colour change of a reagent can be viewed from the exterior of the device. Alternatively, the reagent composition may be impregnated into the device to the extent that colour change is detectable on the exterior of the device (e.g. if the material is sufficiently absorbent to allow fluid to pass to the impregnated reagent).

The combination of urinary directional aid having both disease indicating function and cleansing and antibacterial function which will give improved health (and in particular sexual health and reduction of risk of cervical cancer).

The device according to this embodiment is preferably formed at its proximal end of a rolled edge to reduce abrasion and improve comfort, particularly when the device is formed of a paper or paper-like material.

The dimensions of the device according to this embodiment may be any suitable according to the circumstances. Preferably however, the device is of a length in the range 50 to 150 mm, more preferably 60 to 100 mm and most preferably in the range 65 to 80 mm. Preferably, the proximal aperture is in the range 40 to 75 mm, more preferably 50 to 65 mm and most preferably 55 to 60 mm. The distal aperture is preferably in the range of from 5 to 30 mm, more preferably 10 to 25 mm and most preferably from about 15 to about 20 mm.

An insert for a reusable device may preferably take the shape at the proximal end of the respective proximal aperture of the reusable device or a portion thereof. An insert may comprise of an external lip or sleeve portion around of a portion of the proximal aperture whereby the insert and lip or sleeve thereof engage with the reusable device such that the sleeve or lip slips over the proximal end to cover a portion of the exterior of the reusable device. An insert may be shaped to mimic the whole of internal surface of the reusable device to which it may be fitted, but preferably shaped to only partially cover the internal surface of the reusable device and is preferably shaped so as to provide coverage over the proximal portion (or at least a part thereof) whereby upon removal of the device the urinogenital area can come into contact with the insert and the anti-bacterial or anti-fungal or absorbent portion thereof in order to cleanse the user. For example, an insert into a urinary directional device may form a sleeve over at least the rear portion (in use) of the proximal aperture rim and/or may be shaped to fit at least a rear portion of the proximal portion of the device and provide thereon an absorbent and/or anti-bacterial/antiseptic and/or anti-fungal function whereby on removal of the device by the user, the insert and its hygienic function may be caused to come into contact with or may be conveniently contacted with the urinary area to absorb any residual urine and/or apply a hygienic substance to the urinogenital area about the terminus of the urinary tract. In this way, the insert according to the invention can substantially improve the hygienic use of reusable urinary directional devices.

The insert according to the invention may be shaped or adapted to fit to existing or new urinary directional devices (including, for example, a simple reusable truncated conical device) in order to improve the hygienic performance of the device.

Optionally, an insert may be provided for a device according to the invention which insert comprises a screen or grill which when fitted to the device finds a position in the distal portion of the device and through which fluid must pass in order to pass through the distal aperture (optionally, such a screen or grill may be integrally formed in a device according to the invention instead of being formed only as an insert). The screen or grill may serve for example to retain solids whilst allowing urine fluid to pass through the distal aperture, which solids may be particulates of a predefined minimum size (according to the mesh of the screen). Such a screen or filter may find utility in identify when it is most appropriate to have kidney stones treated, for assessing the progression of kidney calculi or for identifying the presence of other solids in urine.

A screen or grill may alternatively or additionally provide a location for a reagent composition or other health detection indicator. The screen or grill may for example be coated or impregnated with a reagent composition as described above. The screen may be formed of any suitable arrangement of members, which may for example be a plurality of parallel or otherwise oriented members or cross-members. As above, such reagent composition may be specific to a particular substance to be detected or disease or may be a general indicator of a health problem. An insertable screen or grid may provide an additional or complementary test option for a device according to the invention. Optionally, the inserts may be used to provide a range of separate indicator functions which may be selected by the user to fit to their device as required.

As a disposable insert having a screen or grill, there may be a screen portion corresponding to the distal end of the insert and a sleeve portion, which is preferably a short sleeve but of sufficient dimensions to enable the screen portion to be stabilized within the device when fitted.

The device according to the invention is preferably for a single use and as such is made of a disposable material, such as paper, cellulose or other fibrous material or of a plastic material. Preferably, the device is formed from a paper or cellulose material and, for environmental reasons, most preferably paper or other biodegradable material such that it can be flushed away or easily disposed of. In order to maintain robustness and integrity of the device during use, where the device is formed of a core material that can absorb liquid or is biodegradable (such as paper), it is preferable that at least the internal face of the distal portion and preferably also the proximal portion or the whole device, optionally other than an absorbent part of the proximal portion, is made water proof or water repellent, by, for example, compression, coating with a water proof or water repellent material or impregnating with a water proof or water repellent material. Preferably, the necessary degree of water-proofing (in order to assist in a single urination event) is achieved by compression of the paper material forming the device. Accordingly, the device, and in particular, the distal portion of the device repels water allowing urine to pass unimpeded through the device while the device retains its integrity until after use. Preferably, the proximal aperture is defined by a rim which has a rolled edge (especially if the device is formed of a paper or like product) to reduce abrasion and increase the comfort of the device in use.

In one embodiment, the at least part of the proximal portion of the device provides an absorbent and an anti-bacterial/antiseptic and/or anti-fungal function, especially an anti-bacterial or antiseptic function, which function should be hypoallergenic. The absorbent portion may be provided in the proximal portion of the device, for example where the device is formed of a an absorbent core material, by water proofing the device other than in part of the proximal portion which is to remain absorbent. Alternatively, the absorbent portion may be formed by laying on at least part of the internal surface of the proximal portion a layer or coating of an absorbent material, such as an absorbent hydrophilic material, textile or hydrophilic foam, or by coating on at least a portion of the internal surface a porous material such as a coating of silica or clay containing a hydrophilic mordant. Suitable layer or coating materials for use as the absorbent function, include wicking materials such as rayon acetate needled felting, single component fibres (or blended component fibre materials) comprising wool, cotton, rayon, nylon and/or polyester. Other suitable absorbent materials include foamed polymer materials such as polyurethane foams, meshes of synthetic polymers and flexible solids such as latex, but preferably the polymeric foam absorbents are hydrophilic in nature. Swellable polymers, such as polyvinyl alcohol, may also be used to provide the absorbent function. The absorbent function may alternatively be provided by a layer or coating (or impregnation) of an inorganic particulate material which provides a porous material, such as silica, clay, calcium sulfate or calcium carbonate or other such inorganic water absorbing material. Optionally, the absorbent material (such as the inorganic particulate, polymer foam or swellable polymer or even wickable fibre) may comprise or be impregnated with a mordant material capable of trapping the urine (especially the urea and ammonium compounds) thereby improving the effect of the absorbent material and reducing the odour associated with discarded used devices. As a further option, the absorbent layer or coating material may be further impregnated or imbibed with a fragrance, which is optionally released on contact with a liquid, to reduce problems with odour from used devices or to further provide a fragrance release effect for the public or domestic toilet. Where the absorbent function is provided by a layer/layers or a coating of absorbent or wickable material, it is preferably provided in a layer of up to 2.5 mm depth/thickness and more preferably from about 0.5 to about 2 mm.

Such an absorbent function as described above may be utilized to trap urine for testing in a portion of the distal portion as described above.

Optionally, an absorbent coating or portion may be provided on the exterior surface of the device whereby any soiling of the users hand or fingers can be cleansed simply by use of the material.

In a preferred embodiment of the present invention, the device is capable of carrying advertisements primarily on the exterior surface. Typically, this will be achieved by ink-jet printing and as such the device is preferably manufactured from a medium having one surface (which will form the exterior surface of the device) capable of receiving an ink-jet image. Preferably, in order to provide a high quality image, the media from which the device is formed comprises on one surface an ink-jet receiving medium, which optionally may be a porous or a non-porous (i.e. swellable) medium.

Preferably, the media is a porous medium. By utilizing a porous medium, an image may be formed by a high speed ink-jet printing method whilst providing an additional function for the resultant device that the exterior surface of the device is highly absorbent to liquid (especially aqueous fluid) so that any splash or drip of water or urine is rapidly absorbed and not transferred to the user's hands and similarly that any water or urine on the users hands is rapidly absorbed.

Any suitable porous media may be used. Preferably, the porous medium is biodegradable or suitable for being flushed or otherwised disposed of.

The porous medium is typically formed of particulate material, typically inorganic particulate but optionally organic particles, bound by a resin. Any suitable resin may be used, such as polyvinyl alcohol. Optionally, the porous medium is a swellable polymer material having a network of pores formed therein (e.g. by coating the swellable polymer in the presence of a blowing agent which is then activated before curing). In this option, the swellable polymer is preferably a polyvinyl alcohol or other aqueous soluble polymer material.

Suitable such inorganic particulate materials may include, for example, one or more of silica (e.g. colloidal silica), alumina (e.g. alumina sols, colloidal alumina, cationic aluminium oxide or hydrates thereof, pseudoboehmite, etc.), surface-treated cationic colloidal silica, magnesium silicate, aluminium silicate, magnesium carbonate, kaolin, talc, calcium sulfate, barium sulfate, titanium dioxide, zinc oxide, zinc sulfide, zinc carbonate, satin white, diatomaceous earth, calcium silicate, aluminium hydroxide, lithopone, zeolites (such as molecular sieves 3A, 4A, 5A and 13X), hydrated hallocyte and magnesium hydroxide.

The binder may be any suitable binder capable of effectively binding the inorganic particular materials to form a porous ink-receiving layer capable of retaining a pigment or dye, preferably a pigment, to form a printed image having good image properties. Suitable such binders include, for example, one or more of naturally occurring hydrophilic colloids and gums such as gelatin, albumin, guar, xantham, acacia and chitosan and their derivatives, functionalised proteins, functionalised gums and starches, cellulose ethers and their derivatives, such as hydroxyethyl cellulose, hydroxypropyl cellulose and carboxymethyl cellulose, polyvinyl oxazoline and polyvinyl methyloxazoline, polyoxides, polyethers, poly (ethylene imine), poly(acrylic acid), poly(methacrylic acid), n-vinyl amides including polyacrylamide and polyvinyl pyrrolidone, polyethylene oxide and polyvinyl alcohol, its derivatives and copolymers and most preferably polyvinyl alcohol. Preferably, the binder is present in an amount as a ratio of inorganic particulate materials to binder of from 70:30 to 99:1, preferably 75:25 to 96:4 and still more preferably 85:15 to 95:5.

Other components which may be present in the ink-jet receiving medium include, for example, a surfactant and a mordant. Suitable mordants, which may be useful to bind the dye or pigment in the ink in the ink-receiving layer in order to improve still further the image density, include, for example, a cationic polymer, e.g. a polymeric quaternary ammonium compound, or a basic polymer, such as poly(dimethylaminoethyl)methacrylate, polyalkylenepolyamines, and products of the condensation thereof with dicyanodiamide, amine-epichlorohydrin polycondensates, divalent Group 11 metal ions, lecithin and phospholipid compounds or any suitable mordant that is capable of assisting with fixing a dye material transferred to it. Examples of such mordants include vinylbenzyl trimethyl ammonium chloride/ethylene glycol dimethacrylate, poly(diallyl dimethyl ammonium chloride), poly(2-N,N,N-trimethylammonium)ethyl methacrylate methosulfate, poly(3-N,N,N-trimethylammonium)propyl chloride. A preferred mordant would be a quaternary ammonium compound.

Optionally, the medium from which the device is made may comprise, on the side on which an image will be visible, an amorphous hydrated aluminosilicate, such as an allophane, for the reduction of smearing of an image when a printed receiver is stored at high temperatures and humidities, as may typically be the case for the present device which is likely to be used in washrooms.

In the embodiment of the invention, where the media forming the device comprises on one side (the exterior surface) an image-receiving capability, this is preferably achieved by providing a porous ink-receiving layer (as described above) on a suitable support. The non-image receiving surface of the support will typically define the interior surface of the device. Any suitable support in the circumstances may be used, such as a resin-coated support (e.g. resin coated paper), but is preferably a non resin-coated support, more preferably a non resin-coated paper.

In a preferred embodiment, the urinary directional device of the present invention has an image provided on the exterior surface. In a particularly preferable embodiment, due to the moist environment in wash rooms where the device will be used, the image formed is water fast to prevent blurring or smudging of the ink forming the image. A water-fast image may be achieved by any suitable means, but one such method is to utilize an epoxy resin in the image receiving surface of the media from which the device is formed and providing an epoxy curing agent with the ink during printing.

According to this preferred embodiment, in which the device according to the invention carries an image on the exterior surface, which may be a personalized message or advertising, it is preferred that the image is fixed to prevent blurring in a humid atmosphere as may be present in a washroom environment. The exterior surface carrying the image is preferably formed of a porous ink-receiving layer as defined above whereby the image is formed in good colour and resolution characteristics. The interior surface of the device may be compressed paper as discussed above or coated to be at least temporarily water resistant. The interior surface is provided with a cleansing, anti-bacterial/antiseptic and/or anti-fungal function, preferably by coating or impregnating the medium with a composition having the function, most preferably a powdered formulation (increasing the shelf life of the device as compared with liquid formulations which may dry out during storage).

The image may be provided on the exterior surface in any orientation desired. In one embodiment, however, it is preferred that the image is formed on the exterior surface such that it is viewed in the desired manner when the device is orientated distal end upward, such that when stacked distal end upward, it may be viewed at a beneficial angle.

An anti-bacterial or antiseptic or an anti-fungal function is preferably provided in at least part of the proximal portion of the device, on the interior surface of the device, and optionally also on at least part of the exterior surface of the device for contact with the user's fingers. An anti-bacterial material can be applied to an absorbent material (where an absorbent material is included in the device), or to the interior surface of the device, as a surface coating or treatment or can be compounded into the material (e.g. fibres/polymer/pores of an absorbent material). Preferably, commercially available anti-bacterial compositions known and appropriate for use and contact with humans and that are effective against bacterial organisms (e.g. *Escherichia coli, Pseudomonas aeruginosa*)

are utilized. An example of such an anti-bacterial composition is Surfacine® a silver-based anti-bacterial from Surfacine Development Company, Tewksbury, Mass. Alternatively, an antiseptic agent may be used. Any suitable antiseptic agent may be applied, such as DON-2™ available from Cosmic Discovery SDN BHD of Selangor Darul Ehsan, Malaysia, which agent is a mixture of water, silicone oil, cetylpyridinium chloride (a quaternary ammonium salt).

The term "antiseptics" is intended to mean any of a category of antimicrobial substances that inhibits the action of microorganisms, of which examples include (not limited to) chlorhexidine, methylisothiazolone, thymol, .alpha.-terpineol, cetylpyridinium chloride and chloroxylenol. These examples of antiseptics may be used by applying or impregnating an effective amount of one or a combination thereof to the at least part of the proximal portion of the device of the invention.

Preferably, where the device comprises an absorbent function and an anti-bacterial/antiseptic or anti-fungal function on at least a part of the proximal portion, said functions are contiguous. Optionally, the anti-bacterial/antiseptic and/or anti-fungal function is provided by impregnating an anti-bacterial/antiseptic and/or anti-fungal substance or substances into an absorbent material provided.

In any case, the anti-bacterial/antiseptic and/or anti-fungal function should be provided by an agent or substance that is hypoallergenic.

Optionally, the internal portion of the device comprises a cleansing fluid, which is released or applied on contact with the user, such as an encapsulated alcohol formulation.

In a particularly useful embodiment, there is provided an absorbent and cleansing portion on at least a part of the interior proximal portion and on at least a part of the exterior surface of the device, which absorbent and cleansing portions are arranged such that on stacking the absorbent cleansing portion on the internal part of one device contacts with the absorbent cleansing portion on the external portion of another. This has the advantage that where a cleansing fluid or cleansing agent is present, drying or degradation of the material is reduced due to sealing of the area during storage.

A device or insert according to the invention may be prepared, for example, by providing in sheet form a material with which to form the device, impregnating or coating at least a portion of said material with an anti-bacterial/antiseptic or anti-fungal agent, cutting said sheet material and assembling therefrom the device described above. Preferably, the manufacture is carried out in a continuous process in which the sheet material (e.g. paper) is coated, for example on a roll-to-roll process, with an absorbent material (e.g. by coating with a glue according to a specific pattern and then coating with fibres of the absorbent material) and/or an anti-bacterial/antiseptic or anti-fungal agent. Cutting and finishing of the sheet material to form the device of the invention can then be carried out. Preferably, in an embodiment where the device carries and image (e.g. for advertising), the manufacturing method further comprises prior to cutting and finishing of the sheet material, coating onto the sheet material a formulation for forming an image receiving (preferably ink-receiving and more preferably porous) medium, drying the coating and forming thereon (typically also prior to cutting and finishing) one or more desired images (e.g. by high-speed ink-jet printing), typically according to an arrangement of templates on the sheet (as controlled by computer) whereby on cutting and finishing a device with an image on the exterior surface is provided.

Optionally, the information printed on the exterior of the device may be for informing the user what a colour change (or multiple colour changes) is intended to indicate and/or to advise as to the next necessary steps in the event of an indication. Where necessary, there may be printed on the exterior surface an indication comparison strip. The printed information may further provide advertising, which may for example be selected according to the particular form of indication provided by the device. In any case, advertising for private health providers, medicines, sexual health clinics and the like may be provided.

A stacking assembly for the devices of the invention is provided for dispensing of the devices, for example at a domestic or public convenience, in which the devices (or inserts) are stacked one within another to enable the device to be dispensed either distal end first or proximal end first. In one preferred embodiment, the devices are stacked in the dispenser to deliver distal end first. In this embodiment, to maximize the visibility of the images, e.g. advertising, carried on the exterior surfaces of the devices, the stacking assembly is arranged to provide a stack of devices distal end upwards, which may be dispensed from the top by removal of each device from the distal end of the stacking assembly. In this embodiment, it is preferred to utilize devices on which images have been formed to be viewed at the desired orientation when the device is orientated distal end upward.

Preferably, in a stacking assembly of devices carrying advertising or other image or message, the devices are arranged such that more than one advertising message is provided in a stacking assembly, preferably such that a consecutive device in the stacking assembly carries a different advertisement than the preceding device, whereby advertising exposure to a single user is as much as doubled. This may be particularly attractive to advertisers having more than one product.

Optionally, the distal end of the urinary directional device is crimped, such that on application of pressure of fluid during urination the distal aperture opens sufficiently to enable passage of urine through the aperture, whilst enables easier dispensing of the device from a stack thereof. In such a configuration, a reagent composition for use as a health detection indicator may be formed about the distal end of the device whereby it is contacted by a maximal volume of urine and is assured of sufficient contact with urine during use due to the pressure of urine causing the distal end of the device to open.

The device according to the present invention also finds application according to a further embodiment in which it is adapted for use in collecting urination samples (e.g. for medical use). The insert in particular may find application in devices intended for assisting patients in passive urination, whereby the insert allows cleanliness to be maintained during removal of the passive urination device.

In a further aspect of the invention, there is provided a diagnostic device, which device may provide qualitative and/or quantitative diagnosis of diseases or ill-health as described above. According to this aspect of the invention, the device comprises a conduit for the passage of urine and having a proximal end adapted for engagement with the urogenital area, typically the penis, of the user and having a proximal aperture to enable the passage of urine into the conduit and a distal end having a distal aperture to enable the passage of urine from the conduit, further having a distal portion characterized by providing for the passage of a stream of urine and a proximal portion, which during urination does not come into substantial contact with the stream of urine, said device characterized in that it is provided with a health detection indicator capable of indicating abnormalities in urine indicative of disease or health-related conditions, which health detection indicators is preferably one or more reagent compositions coated onto or impregnated into the distal portion of the device, the reagent compositions being capable of indicating one or more abnormalities in the urine that are indicative of disease and/or health-related conditions. The reagents may for example be any known in the art and capable of use in diagnosis, and preferably include those for detecting the substances or components defined above and preferably indicative of diseases or illnesses, such as those defined above. Where the device is for qualitative assessment, the reagent composition should be formed on the device such as to indicate, e.g. by colour change, a certain minimum level of substance to be identified, which level is indicative of a problem. Where the device is for quantitative assessment, the reagent composition should be formed on the device such that on passage of urine and indication is given as to the relative amounts of substance to be identified, e.g. by variable colour change, as is known in the art for use on urinalysis sticks. In the quantitative diagnostic device, the device may further be provided with a diagnostic chart to enable the colour change resulting from the test to be rapidly and conveniently analysed as to the extent of colour change and corresponding quantitative assessment. This chart may be provided, for example, in the interior of the device.

Optionally, the health detection indicator, typically being a reagent formulation, is provided impregnated into a portion of the distal portion of the device designed as a form of reservoir for conducting the test. This may be achieved by means of a fluid absorbent area such as by padding material, such as described above, or, for example, by multiple microfluidic pores formed on the internal surface over a specified area in order to control the volume of urine from which the indicative test result is being achieved. According to this embodiment, the fluid reservoir may be a wicking material or other such reservoir capable of absorbing a predetermined quantity of fluid and impregnated with a predetermined amount of one or more reagent composition in quantities suitable for determining quantitative analysis of the substance-content of the quantity of fluid absorbed and indicating the same, e.g. by way of colour change or colour gradient indicator.

Optionally, the device according to this aspect is formed of a material suitable for. Accordingly, the device may be a re-usable device and so formed of suitable materials for reuse, such as plastics. In this case, the diagnostic chart may optionally be provided on the reusable device or on a disposable insert. Preferably, when a reusable device is provided, the health detection indicator, such as the reagent composition, is provided on a disposable insert such as in the manner provided above, which disposable insert may preferably comprise a reservoir for capture of fluid for quantitative analysis. In a still further option, where the device is reusable, the reagent composition may be applied directly to the distal portion of the device for each diagnostic use and removed after use ready for reapplication of reagent composition for further diagnostic use. The device should otherwise be configured where appropriate and suitable in the context in any other way as defined above.

In one embodiment of the invention, it is provided with a medical function relevant to the reduction of cervical cancer risk factors such as an anti-bacterial function effective against *Chlamydia* infection and/or an anti-viral function effective against HPV (especially types 16, 18 and/or 31) and an indicator capable of indicating urine abnormalities associated with such bacterial or viral infections (e.g. the presence of antibodies or antigen or other indicators). Thus a male users likelihood of having an infection that is a risk factor or co-factor in the risk of a female sexual partner contracting cervical cancer may reduced (by improved hygiene and/or early detection) through occasional or regular use of the device. Accordingly, there is provided a method of reducing bacterial or viral sexually transmitted infection risk by a male the method comprising regular use of a device hereinbefore defined. And, there is provided a method of reducing the incidence of cervical cancer in a defined area by distribution through the population in said area and use of a device as hereinbefore defined, which device is configured for enhanced hygiene and health indication for factors associated with cervical cancer risk factors.

The invention will now be described in terms of a preferred embodiment, without limitation as to the scope of the invention, with reference to the attached figures.

With reference to FIG. 1, a directional urinary device consists of a truncated conical (or frusto-conical) funnel 1 having a conduit therethrough defined by the interior of the funnel 1 and a larger diameter proximal aperture 3 adapted to fit about the tip of the penis of a user and a smaller diameter distal aperture 5 for the passage of urine out of the conduit. The device is defined as having a distal portion 7, through which urine will pass to the distal aperture 5, and a proximal portion 9, the border between the distal portion 7 and the proximal portion 9 being about the area where the tip of the penis engages with the device in use. Typically, the surface of the proximal portion 9 will not come into substantial contact with urine during urination although leakage and spillage during or immediately after urination may cause wetting of the proximal portion 9. The proximal portion is characterized by having coating 11 (hatched area), which may have absorbency and/or anti-septic or anti-fungal properties. The distal edge of the coating 11 may define or extend beyond the border of the distal portion 7 and the proximal portion 9 of the device, or it may be located and specific areas within the proximal portion 9. In the FIGS. 1, 2 and 4, the coating 11 is shown as covering the internal circumference of the device and, as can be seen in FIG. 4, may be several millimeters thick, which depending upon the material from which it is made provides extra absorbency and also comfort and improved engagement for the wearer. A reagent composition coating 12 may be formed in the distal portion 7 to provide a passive health detection indication by indicating through a colour change the presence of levels of one or more substances indicative of disease or ill-health. The reagent composition may define an internal circumference of the device as illustrated in FIG. 4. In FIG. 4, it can be seen that the proximal aperture 3 is defined by a roiled edge 13, which provides structural integrity to the device and assists in maintaining the shape of the proximal aperture 3 during stacking and in use as well as improve the strength of the device and prevent it from collapsing during use. The device may be manufactured to the required size, but according to the Figures, has a length 15 of about 70 mm, a proximal diameter 17 of about 58 mm and a distal diameter 19 of about 5 mm.

The device 1 may be manufactured by coating onto a web of the material from which the device 1 is made a coating 11 in a pre-determined shape, cutting the material such that it can be assembled into a truncated conical shape and sealed along edges 21 such that the coating 11 is formed in the desired configuration.

FIG. 5 shows a view of a disposable insert 23 having a screen 25 at its distal end and a sleeve 27, which insert is configured to fit within a device 1 in order to provide a screen in the distal portion 7. This screen may be coated with a reagent composition for use as a passive health detection indicator or provided with a mesh to trap predetermined sized solid particulates.

In use, the device 1 is engaged with the tip of the user's penis such that the urethral passage terminates in an area bordering or above the distal portion 7. During urination, the device 1 is directed as required to enable urine to pass through the distal aperture 5 to the target, e.g. urinal or toilet bowl. Once urination is complete, the device 1 is removed whilst allowing the tip of the penis to brush across the coating 11 which draws up residual urine on the tip of the penis and/or applies an anti-bacterial to the penis to improve hygiene. By locating the absorbent and/or anti-septic or anti-fungal coating in the proximal zone, preferably for positioning at the underside of the penis, improved absorbency of residual urine (preventing later spillage, dripping and soiling of hands or clothing) and optionally application of an anti-bacterial substance (to improve hygiene of the user) can be achieved simply through the action of removal of the device 1. The device 1, can then be disposed of in an hygienic matter in a conveniently provided refuse container.

The invention has been described with reference to a preferred embodiment. However, it will be appreciated that variations and modifications can be effected by a person of ordinary skill in the art without departing from the scope of the invention.

What is claimed is:

1. A urinary directional device for improving the directional urination of a male user, said device comprising a conduit for the passage of urine and having a proximal end adapted for engagement with the penis of the user, said device having a distal portion which provides for the passage of a stream of urine and a proximal portion which does not come into substantial contact with the stream of urine, said device having an interior surface and an exterior surface, the device being characterized in that the interior surface provides in at least part of the proximal portion an absorbent function and contiguous therewith one or more of an anti-bacterial or anti-septic or an anti-fungal function whereby the penis of the user can be cleansed by wiping on the interior surface of the device after urination, further characterized in that the distal portion of the device comprises a health detection indicator capable of indicating abnormalities in urine indicative of disease or health-related conditions, wherein at least the interior surface of the distal portion is adapted to repel water so as to allow urine to pass unimpeded through the device whilst the device retains its integrity for at least one use, and wherein the health detection indicator is spatially separate from and distal to the antiseptic, antibacterial or antifungal function.

2. The urinary directional device according to claim 1, wherein the health detection indicator is provided by one or more reagent compositions impregnated into and/or coated onto the interior surface of the distal portion of the device.

3. The urinary directional device according to claim 1, wherein the health detection indicator is capable of detecting the presence of one or more of glucose, ketones, blood, haemoglobin, protein, nitrite, urobilinogen, bilirubin, leukocytes, pH, specific gravity, antibodies associated with infection, and hormones associated with the presence of disease in a body, each at a level indicative of health abnormalities.

4. The urinary directional device according to claim 1, which provides an indication for further investigation as to the presence in the user of one or more of diabetes, liver dysfunction, liver disease, liver failure, renal glycosuria, insufficient food intake, kidney damage, urinary tract infection, kidney or bladder calculi, myocardial infarction, muscle damage, bacterial infection, haematoma, cystitis, testicular cancer, prostate cancer, cancer, and HIV.

5. The urinary directional device according to claim 1, wherein the device is frusto-conical in shape.

6. The urinary directional device according to claim 1, wherein the one or more of an anti-bacterial or antiseptic or anti-fungal function is provided by a coating formed on the interior surface of the device and whereby the penis of the user can be cleansed by wiping with the at least part of the proximal portion after urination.

7. The urinary directional device according to claim 1, wherein the one or more of an anti-bacterial or antiseptic or anti-fungal function is provided by an anti-bacterial or anti-septic or anti-fungal substance or composition impregnated into the interior surface of the device and whereby the penis of the user can be cleansed by wiping with the at least part of the proximal portion after urination.

8. The urinary directional device according to claim 7, wherein the device is provided with an anti-bacterial or antiseptic function by impregnation of an antibacterial or antiseptic powder into the interior surface of the device.

9. The urinary directional device according to claim 1, wherein the health detection indicator is provided by one or more reagent compositions impregnated into and/or coated onto the interior surface of the distal portion of the device to form a ring of the one or more reagent compositions.

10. The urinary directional device according to claim 1, wherein the device consists of a stiffened paper which is provided with a water-proofed or water resistant surface.

11. The urinary directional device according to claim 1, wherein a circumference defining a proximal aperture is provided with a rolled edge.

12. The urinary directional device according to claim 1, wherein at least a part of the external surface of the device provides an absorbent and/or anti-bacterial function whereby the hand or fingers of the user can be cleansed by the action of applying and removing the device.

13. The urinary directional device according to claim 1, wherein the exterior surface of the device is formed of a material capable of performing as an image receiving medium for the purpose of carrying advertising, images or personalized messages, or health-related information, or diagnostic information.

14. The urinary directional device according to claim 13, wherein the exterior surface of the device is a porous media which carries a water-fast ink-jet image and is capable of absorbing aqueous fluid on contact.

15. A stacking assembly of the device as defined in claim 1, said assembly comprising a dispensing component for dispensing said devices and a plurality of said stacked devices.

16. The urinary directional device according to claim 1, wherein the absorbent function is providing by laying on the internal surface a layer of absorbent material.

17. The urinary directional device according to claim 16, wherein the internal surface of the device comprises an anti-bacterial function, which is provided by applying an anti-bacterial material to the absorbent material.

18. The urinary directional device as claimed in claim 1, wherein the at least part of the proximal portion of the interior surface of the device which provides an antibacterial or antiseptic function is provided by an antimicrobial substance that inhibits the action of microorganisms.

19. The urinary directional device according to claim 1, wherein the whole device, other than the absorbent part of the proximal portion, is made water proof or water repellent by compression, coating with a water proof or water repellent material, or impregnating with a water proof or water repellent material.

20. A method of manufacturing a urinary directional device for improving the directional urination of a male user, said device comprising a conduit for the passage of urine and having a proximal end adapted for engagement with the penis of the user, said device having a distal portion which provides for the passage of a stream of urine and a proximal portion which during urination does not come into substantial contact with the stream of urine, said device having an interior surface and an exterior surface, the device being characterized in that the interior surface provides in at least part of the proximal portion an absorbent function and contiguous therewith one or more of an anti-bacterial or antiseptic or an anti-fungal function whereby the penis of the user can be cleansed by wiping on the interior surface of the device after urination and in that at least the interior surface of the distal portion is adapted to repel water so as to allow urine to pass unimpeded through the device whilst the device retains its integrity for at least one use, said device further comprising in the distal portion a health detection indicator capable of indicating abnormalities in urine indicative of disease or health-related conditions wherein the health detection indicator is spatially separate from and distal to the antiseptic, antibacterial or antifungal function, said method comprising providing in sheet form a material with which to form the device, impregnating or coating at least a portion of said material with an anti-bacterial or anti-fungal agent, cutting said sheet material, providing an absorbent function to the material, providing a health detection indicator spatially separate from and distal to the antiseptic, antibacterial or antifungal function to the material and assembling therefrom the device.

\* \* \* \* \*